United States Patent [19]

Burdorf et al.

[11] Patent Number: 5,795,688
[45] Date of Patent: Aug. 18, 1998

[54] PROCESS FOR DETECTING DEFECTS IN PHOTOMASKS THROUGH AERIAL IMAGE COMPARISONS

[75] Inventors: James Burdorf, Meridian; Christophe Pierrat, Boise, both of Id.

[73] Assignee: Micron Technology, Inc., Boise, Id.

[21] Appl. No.: 696,652

[22] Filed: Aug. 14, 1996

[51] Int. Cl.⁶ .................. G01N 21/00; G03F 9/00
[52] U.S. Cl. ............... 430/30; 430/5; 356/237; 382/144
[58] Field of Search .............. 430/5, 30; 382/144; 356/237

[56] References Cited

U.S. PATENT DOCUMENTS 4,809,341  2/1989  Matsui et al. .................. 382/144
5,481,624  1/1996  Kamon .......................... 382/144

FOREIGN PATENT DOCUMENTS 138639  4/1985  European Pat. Off. .......... 382/144

Primary Examiner—Christopher G. Young
Attorney, Agent, or Firm—Arnold, White & Durkee

[57] ABSTRACT

The present invention provides a process for performing automatic inspection of advanced design photomasks. In a preferred embodiment, an aerial image of a portion of a photomask is generated. A simulated image corresponding to original pattern data is also generated. The aerial image and simulated image are then compared and discrepancies are detected as possible defects.

24 Claims, 2 Drawing Sheets

PROCESS FOR DETECTING DEFECTS IN PHOTOMASKS THROUGH AERIAL IMAGE COMPARISONS

This invention was made with government support under Contract No. MDA 972-92-C-0054 awarded by Advanced Research Projects Agency (ARPA). The government has certain rights in this invention.

BACKGROUND OF THE INVENTION

The present invention relates to processes for inspecting photomasks to detect defects. More particularly, the present invention relates to an automatic inspection system for detecting defects in photomasks.

Advances in capacity in semiconductor chips have generally been the result of decreases in the size of features on a chip. The lateral dimensions of features are generally defined by photolithographic techniques in which a detailed pattern is transferred to a photoresist by shining light through a photomask or reticle.

In recent years, phase shifting masks have been developed to improve photolithographic processes. Phase shifting masks increased image contrast and resolution without reducing wave length or increasing numerical aperture. These masks also improve depth of focus and process latitude for a given feature size.

With phase shift photolithography, the interference of light rays is used to overcome the problems of detraction and improve the resolution and depth of optical images projected onto a target. With this technology, the phases of the exposure light at the target is controlled such that adjacent bright areas are preferably formed 180° out of phase with each other. Dark regions are thus produced between the bright areas by destructive interference even when detraction would otherwise cause these areas to be lit. This technique improves total resolution at the target.

Another method that has been developed to produce masks for use in the fabrication of semiconductors containing small features is optical proximity effect correction "OPC"). In this method, changes are made to the binary mask's layout so that it will print more clearly. Because of the limited resolution of the current photolithographic tools (i.e., steppers), the patterns defined on the photomask are transferred into the resist on the wafer with some distortions referred to as optical proximity effects. The main consequences in term of line width control are: corner rounding, difference between isolated and semi-isolated or dense patterns, lack of CD linearity or where small features print even smaller than their expected size compared to large features, and line end shortening where the length of a line having a small line width becomes smaller than its expected size.

Moreover, optical proximity effects are convoluted with subsequent processing step distortions like resist processing, dry etch proximity effects and wet etch proximity effects. In order to achieve a sufficient line width control at the wafer level, the mask designs are corrected for proximity effects, namely re-entrant and outside serifs are used to correct rounding and the edges of the patterns are moved to correct line width errors. Another technique consists in adding small, non-printing features, referred to as subresolution features, in order to correct line width errors. In some cases, these features can also improve the process latitude of the printed resist patterns.

Printable defects in photomasks and reticles have historically been a source of defects that have reduced die yields. With current photolithographic techniques, printable defects in the photomasks, are repeated many times over the surface of a semiconductor wafer and can result in substantial yield losses. Accordingly, it is important to detect and correct as many defects as possible in the photomasks.

Defects in photomasks can arise from many different sources. For example, certain defects such as bubbles, scratches, pits and fractures can be contained in the raw glass substrates. Defects can also be formed in the chrome layer by particulate inclusions, pin holes or voids, and excess material.

As advances have been made in photomask design such as phase shifting and OPC, it has become harder to detect defects in the photomasks. However, defect detection and correction has become increasingly important. Previously, masks were checked by exposing and developing an image on a resist layer on a plain quartz wafer. The resulting pattern was then inspected. However, there was no die-to-database inspection with this system.

Automatic photomask defect detection systems have been developed and are commercially available. These include systems such as the KLARIS system by KLA Instruments Corp. and the Chipcheck system by Cambridge Instruments. Inspection tools such as KLA and Orbot systems are also available for die-to-die inspection of the printed image on wafers. These systems are limited by the fact that the inspection is performed at 1×(versus 4×or 5×for most advanced reticles). The maximum allowable defect size is smaller and a complete inspection is not possible in the case of a single die reticle as die-to-database capability is not available on these systems.

In the KLA system, light is transmitted through the photomask and detected by a CCPD image sensor. This image is then compared to the image from a database or compared to the image from another die on the mask. If one comparison of a die to the database is performed, the remaining comparisons on the mask can all be die-to-die inspections that relate back to the initial comparison.

These prior art systems are generally limited to basic mask designs and have limited capability of checking advanced designs such as those containing optical proximity effect corrections and phase shifting layers.

Because of the importance in detecting and correcting photomask defects, it would be a significant advancement in the art to provide an automatic process for detecting defects in advanced photomask designs. Such a process is disclosed and claimed herein.

SUMMARY OF THE INVENTION

The present invention provides an automatic process for detecting printable defects in masks. The invention is particularly useful in analyzing advanced photomask designs such as those which include optical proximity effect corrections and phase shifting layers.

In a preferred embodiment, a mask design is generated from a binary mask layout. The mask design is then used to generate a photomask such as by suitably etching a chrome layer on a quartz plate. The present invention provides a process for detecting any defects that are formed in the photomask. In a preferred embodiment, an aerial image of the photomask is generated. This is then compared with a simulated image of the binary mask layout which has been adjusted to account for expected distortions and corner rounding caused by image processing of the mask and wafer. Any discrepancies between the aerial image and the simulated image are likely due to defects in the photomask.

In a second preferred embodiment, the aerial image of the photomask is compared with a simulated aerial image of the mask design. Again, any discrepancies between these two images are likely due to defects in the photomask.

DETAILED DESCRIPTION OF THE PREFERRED EMBODIMENTS

The present invention provides a process for performing an automatic inspection of advanced design photomasks to detect printable defects which might cause fatal flaws in semiconductor dies. The invention is best understood by reference to the attached drawings in which like parts are designated with like numerals.

Figure 1:
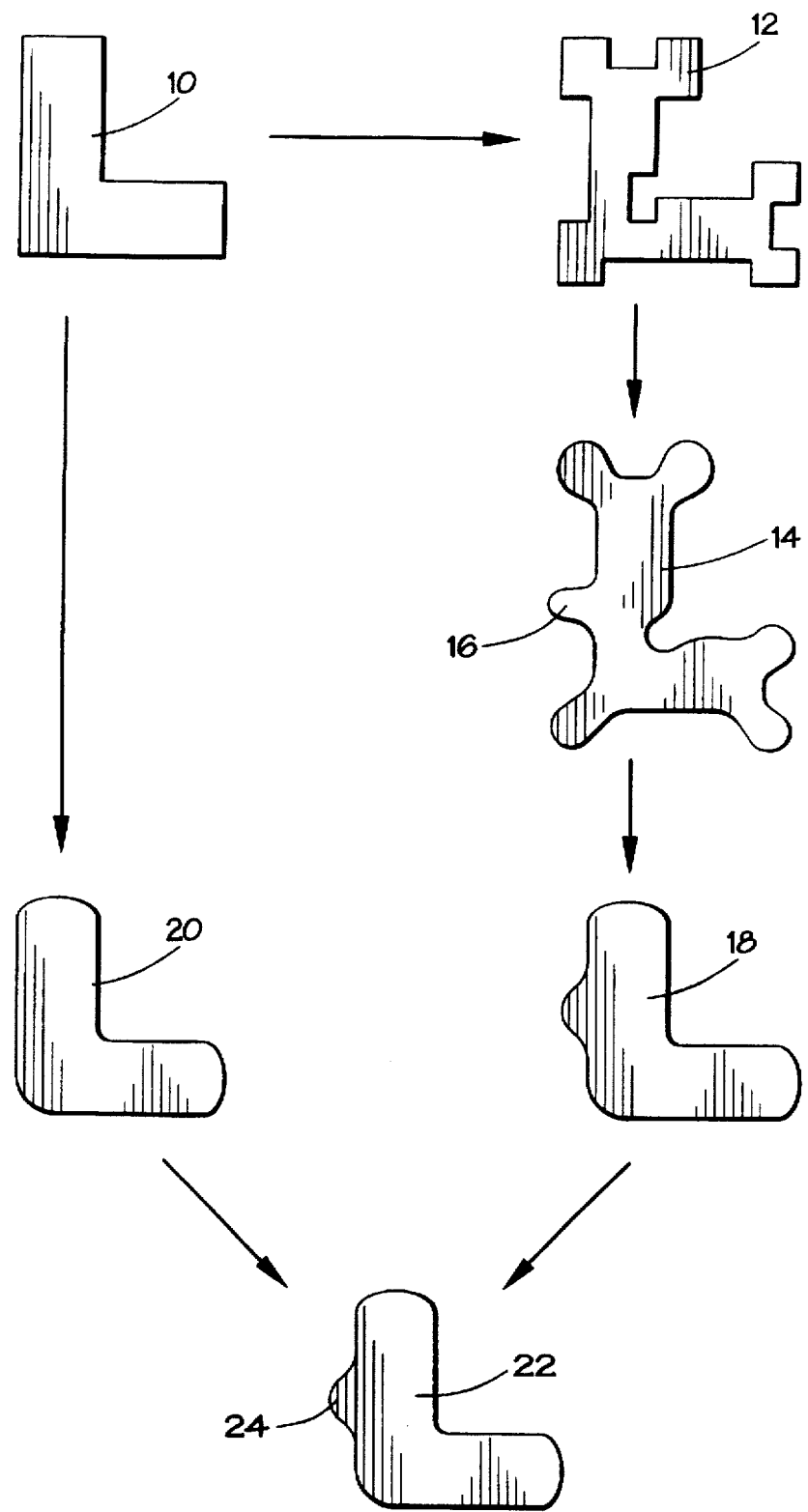
FIG. 1 is a schematic illustration of a feature of a photomask design illustrated at different stages according to a first embodiment of the present invention.

Referring first to FIG. 1, a feature of a semiconductor mask design is generally designated at 10. Feature 10 forms part of a binary mask layout. From this layout, features on an advanced mask design are generated. Feature 12 corresponds to feature 10 but is obtained by applying optical proximity effect correction techniques to feature 10. Feature 12 is then used to generate a corresponding feature on a photomask.

Feature 14 corresponds to feature 12 as it appears in the chrome on the photomask. During fabrication, a defect 16 was formed in the design. Defect 16 comprises excess chrome which remains on the quartz plate. However, it will be appreciated by those skilled in the art that the process of the present invention can also be used to detect other types of defects such as missing chrome, contamination, glass damage, phase defects, transmission errors and even poor repairs made to a defective mask.

In order to detect any defects, an aerial image 18 is generated from feature 14 on the photomask. Aerial images can be generated using a system comparable to the commercially available MSM-100 aerial image measurement system manufactured by Carl Zeiss, Inc. This system is set up to analyze actual masks under optical conditions that are essentially equivalent to those of a stepper of interest, but greatly magnified. As the exposure light is shown through the mask and magnified, a UV sensitive CCD camera is used for data capture.

A simulated image 20 of feature 10 is also generated and takes into account expected distortions and corner rounding due to image processing of the mask and wafer.

Image 20 can also be the result of the convolution of feature 10 with some convolution function(s) representing, but not limited to, the aerial image, the mask fabrication process and OPC corrections. For example, the aerial image can be generated by various software programs such as FAIM produced by Vector Technologies, DEPICT produced by TMA, and SPLAT produced by The University of California, Berkeley.

Aerial image 18, which is generated using a threshold such that dimensions of image 18 match the dimensions of image 20, is then compared to simulated image 20. Incongruity 24, which corresponds to defect 16, will be identified during the comparison as a discrepancy between the two images.

Figure 2:
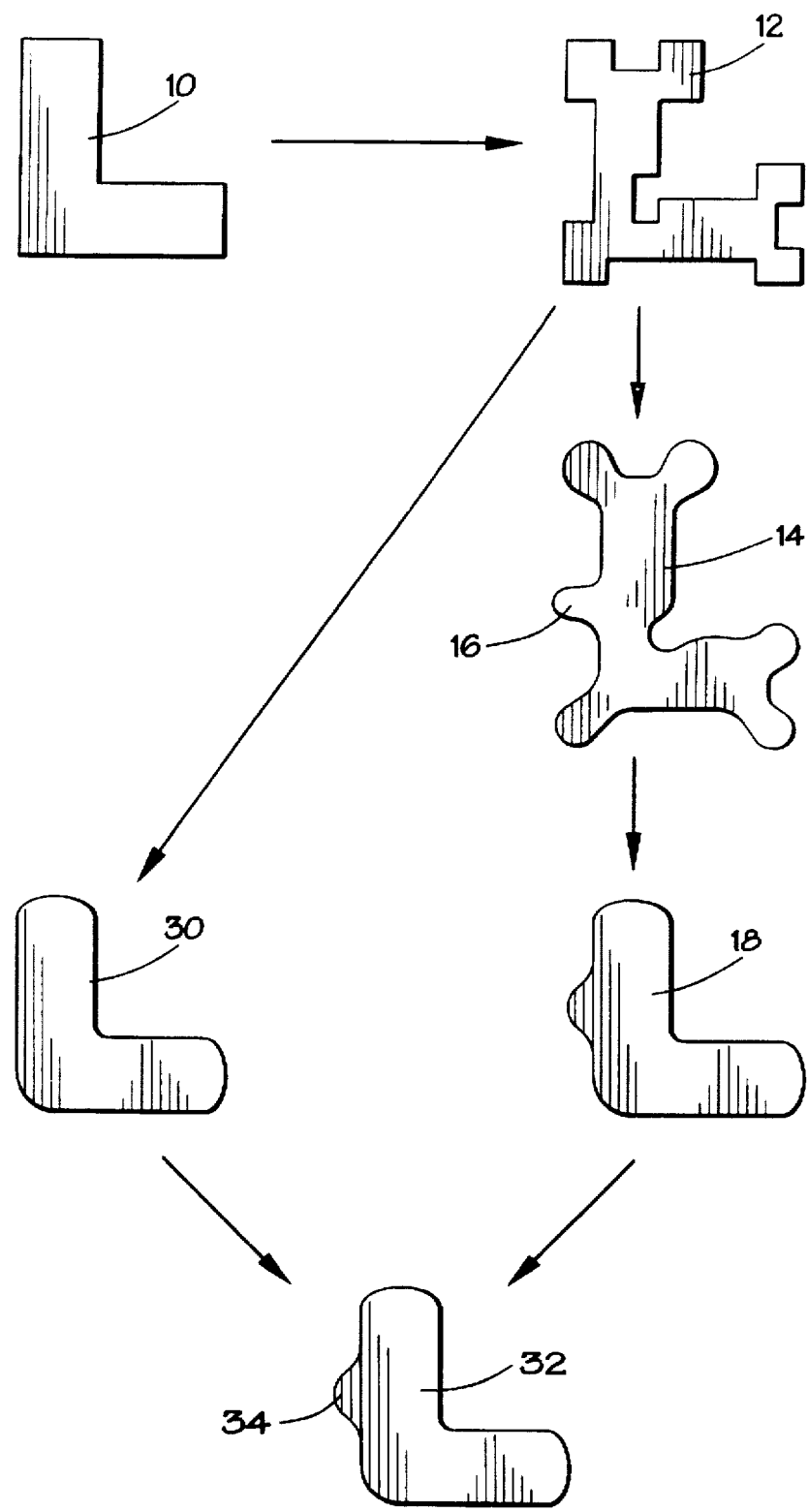
FIG. 2 is a schematic illustration of a feature of a photomask design illustrated at different stages according to a second preferred embodiment of the present invention.

Reference is next made to FIG. 2 which illustrates a second preferred embodiment of the present invention. In this embodiment, a feature 10 of binary mask design is again used to generate a mask design feature 12. This mask design is then used to generate feature 14 on a photomask and an aerial image 18 is generated from the image on the photomask.

However, in this embodiment, simulated image 30 is generated as a simulated aerial image of mask design image 12. Aerial image 18 is then compared to this simulated image 30 to obtain a comparison 32 where any incongruities 34 will appear as discrepancies between the two images. Image 30 can also be the result of the convolution of feature 10 with some convolution function(s) representing, but not limited to, the aerial image, the mask fabrication process, OPC corrections, etc.

While the invention has been described with respect to mask designs using optical proximity effect correction techniques, it will be appreciated by those skilled in the art that it can also be applied to other advanced mask designs such as those using phase shifting layers. The invention can be used either to analyze known defects or to do an automated inspection over an entire mask surface. Additionally, while the above description has been limited to the analysis of a single feature, it will be appreciated that blocks of multiple features can be analyzed.

In addition to photomasks, the present invention can be used for x-ray masks, stencil masks for ion projection lithography, masks for electron beam projection lithography, etc. The techniques of the present invention can also be applied to imaging systems other than those used in the manufacture of integrated circuits.

While the invention has been described with respect to the presently preferred embodiments, it will be appreciated by those skilled in the art that changes and modifications could be made to the disclosed embodiments without departing from the spirit or scope of the invention. For example, the inspection technique and aerial images could be performed out of focus in order to detect defects that mainly print out of focus such as phase defects. Additionally, other techniques of mathematical processing of the data can be used to generate images 20 and 30. Further, the simulated image of the mask can be generated during inspection or a portion of the simulation can be performed before inspection and the remainder during inspection. Accordingly, all changes or modifications which come within the meaning and range of equivalency of the claims are to be embraced within their scope.

We claim:

1. A process for detecting defects in masks comprising:
    generating an aerial image of a portion of a mask;
    generating a simulated image corresponding to original pattern data used to create said mask taking into account expected distortions and corner rounding due to image processing; and
    comparing said aerial image to said simulated image.

2. A process for detecting defects in masks as defined in claim 1 wherein said simulated image is obtained by generating a simulated aerial image of a mask design used to generate a portion of the mask with which it is compared.

3. A process for detecting defects in masks as defined in claim 1 wherein said mask is generated using proximity effect correction techniques.

4. A process for detecting defects in masks as defined in claim 3 wherein said mask is generated using optical proximity effect correction techniques.

5. A process for detecting defects in masks as defined in claim 3 wherein said mask is generated using x-ray proximity effect correction techniques.

6. A process for detecting defects in masks as defined in claim 3 wherein said mask is generated using ion beam proximity effect correction techniques.

7. A process for detecting defects in masks as defined in claim 3 wherein said mask is generated using e-beam proximity effect correction techniques.

8. A process for detecting defects in masks as defined in claim 1 wherein said mask includes phase shifting techniques.

9. A process for detecting defects in masks as defined in claim 1 wherein said mask includes proximity effect correction techniques and phase shifting techniques.

10. A process for detecting defects in masks as defined in claim 1 wherein said masks are used in the manufacture of integrated circuits.

11. A process for detecting defects in masks as defined in claim 1 wherein said mask comprises an x-ray mask.

12. A process for detecting defects in masks as defined in claim 1 wherein said mask comprises a stencil mask for ion projection lithography.

13. A process for detecting defects in masks as defined in claim 1 wherein said mask comprises a mask for electron beam projection lithography.

14. A process for detecting defects in masks as defined in claim 1 wherein said aerial image and said simulated image are generated out of focus.

15. A process for detecting defects in photomasks comprising:

generating an aerial image of a portion of a photomask;

generating a simulated image corresponding to original pattern data used to create said photomask taking into account expected distortions and corner rounding due to image processing; and comparing said aerial image to said simulated image.

16. A process for detecting defects in photomasks as defined in claim 15 wherein said simulated image is obtained by generating a simulated aerial image of a mask design used to generate the portion of the photomask with which it is compared.

17. A process for detecting defects in photomasks as defined in claim 15 wherein said photomask is generated using optical proximity effect correction techniques.

18. A process for detecting defects in photomasks as defined in claim 15 wherein said photomask includes phase shifting techniques.

19. A process for detecting defects in photomasks as defined in claim 15 wherein said photomask includes proximity effect correction techniques and phase shifting techniques.

20. A process for detecting defects in photomasks as defined in claim 15 wherein said aerial image and said simulated image are generated out of focus.

21. A process for detecting defects in masks comprising:

generating an aerial image of a portion of a mask;

generating a simulated aerial image of a mask design used to generate said portion of said mask; and comparing said aerial image to said simulated aerial image.

22. A process for detecting defects in masks as defined in claim 21 wherein said mask is generated using proximity effect correction techniques.

23. A process for detecting defects in masks as defined in claim 21 wherein said mask includes phase shifting techniques.

24. A process for detecting defects in masks as defined in claim 21 wherein said mask includes proximity effect correction techniques and phase shifting techniques.

* * * * *

UNITED STATES PATENT AND TRADEMARK OFFICE
CERTIFICATE OF CORRECTION

PATENT NO. : 5,795,688

DATED : August 18, 1998

INVENTOR(S) : Burdorf et al.

It is certified that error appears in the above-identified patent and that said Letters Patent is hereby corrected as shown below:

Column 1, line 28, detraction should be defraction.

Column 1, lines 35 and 36, detraction should be defraction.

Column 2, line 27, 4xor    5xfor should be 4x or and 5x for.

Signed and Sealed this

Twelfth Day of January, 1999

Attest:

*Attesting Officer*            Acting Commissioner of Patents and Trademarks